US00PP10256P

United States Patent [19]

Cosner et al.

[11] Patent Number: Plant 10,256

[45] Date of Patent: Feb. 24, 1998

[54] DOUBLE IMPATIENS PLANT NAMED 'TIOGA TANGERINE'

[76] Inventors: Harlan B. Cosner; Sue L. Cosner, both of P.O. Box 173, Broadbent, Oreg. 97414

[21] Appl. No.: 772,490

[22] Filed: Dec. 23, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of Double Impatiens plant named 'Tioga Tangerine', characterized by its large orange flowers; flowers held above or beyond the foliage; consistently double and symmetrical flower form; numerous flowers per plant; freely branching, dense plant habit; upright and mounded plant habit, triangular in shape; and dark green foliage.

1 Drawing Sheet

The present invention relates to a new and distinct cultivar of Double Impatiens plant, botanically known as *Impatiens walleriana*, and hereinafter referred to by the cultivar name 'Tioga Tangerine'.

The new cultivar is a spontaneous mutation of a unnamed proprietary seedling selection. The new cultivar was discovered and selected by the inventors in a controlled environment in Coquille, Oreg., in June, 1993, as a single lateral branch of a plant of the unnamed proprietary seedling selection. This single lateral branch was chosen as it produced fully double flowers. Asexual reproduction of the new cultivar by terminal cuttings taken at Coquille, Oreg., has shown that the unique features of this new Double Impatiens are stable and reproduced true to type in successive generations of asexual reproduction.

The following traits have been repeatedly observed and are determined to be the unique characteristics of 'Tioga Tangerine'. These characteristics in combination distinguish the new Double Impatiens as a new and distinct cultivar:

1. Large orange flowers.
2. Flowers held above or beyond the foliage.
3. Consistently double and symmetrical flower form.
4. Numerous flowers per plant.
5. Freely branching, dense plant habit.
6. Upright and mounded plant habit, triangular in shape.
7. Dark green foliage.

In contrast to plants of the new Double Impatiens, plants of the parent proprietary seedling selection had semi-double flowers with reproductive organs and capable of producing seed. In addition, plants of the new Double Impatiens are more compact and more freely branching than plants of the parent proprietary seedling selection.

The new Double Impatiens is similar in flower color to the Double Impatiens cultivar Rosebud Orange (not patented). However in side-by-side comparisons in Coquille, Oreg., under commercial practice, plants of the new Double Impatiens differed from plants of the cultivar Rosebud Orange in the following characteristics:

1. Plants of the new Double Impatiens are taller and more vigorous than plants of the cultivar Rosebud Orange.

2. Plants of the new Double Impatiens are upright, mounded and triangular in shape whereas plants of the cultivar Rosebud Orange have an open plant habit and cascade downwards.

3. Plants of the new Double Impatiens are more freely branching and are denser than plants of the cultivar Rosebud Orange.

4. Plants of the new Double Impatiens have shorter but thicker lateral branches than plants of the cultivar Rosebud Orange.

5. Leaves of plants of the new Double Impatiens are longer and narrower with longer petioles than leaves of plants of the cultivar Rosebud Orange.

6. Flowers of plants of the new Double Impatiens face upward or outward whereas flowers of plants of the cultivar Rosebud Orange face outward or downward as peduncles of plants of the cultivar Rosebud Orange are weaker and longer than peduncles of the new Double Impatiens.

7. Flowers of plants of the new Double Impatiens are smaller than flowers of the cultivar Rosebud Orange.

8. Flower spurs of plants of the new Double Impatiens are shorter than flower spurs of plants of the cultivar Rosebud Orange. In addition, the flower spur color is different.

A detailed comparison of plants of the new Double Impatiens and the cultivar Rosebud Orange appears in Chart A at the end of the specification.

The new Double Impatiens has not been observed under all possible environmental conditions. The phenotype may vary significantly with variations in environment such as temperature and light level, without, however, any variance in genotype.

The accompanying colored photographs illustrate the overall appearance and flower color of the new Double Impatiens, showing the colors as true as it is reasonably possible to obtain in colored reproductions of this type.

The first photograph comprises a side perspective view of a typical plant of the new Double Impatiens.

The second photograph comprises a side perspective view of typical plants of the cultivar Rosebud Orange (left) and the new Double Impatiens (right) showing the differences in plant and flowering habit. Flower and foliage colors in the photographs may appear different from the actual colors due to light reflectance.

The following observations, measurements, values, and comparisons describe plants grown in Coquille, Oreg., grown under double layer of polyethylene with day temperatures ranging from 23 to 30C and night temperatures ranging from 10 to 18C, and light levels ranging from 3,000 to 5,000 footcandles.

In the following description, color references are made to The Royal Horticultural Society Colour Chart except where general terms of ordinary dictionary significance are used.

Botanical classification: *Impatiens walleriana* cultivar 'Tioga Tangerine'.

Parentage: Spontaneous mutation of a unnamed proprietary seedling selection.

Propagation:

*Type cutting.*—Terminal cuttings.

*Time to initiate roots.*—About 14 days at a temperature of 20C.

*Rooting habit.*—Numerous, fibrous, and well-branched.

Plant description:

*Form.*—Upright and mounded plant form, triangular shape.

*Growth habit.*—Vigorous. Dense and bushy growth. Flowers above or beyond the foliage. Suitable for 10 to 25-cm containers.

*Plant height.*—About 25 cm.

*Branching habit.*—Freely branching with about eight lateral branches, branches very strong.

*Lateral branches.*—Size: Length: About 20 cm. Diameter: About 1.3 cm. Internode length: About 2.5 cm. Color: 146C with faint red (59A) spots and areas at nodes.

*Foliage description.*—Leaves simple, generally symmetrical, abundant, alternate, and flat in aspect. Size, largest leaves: Length: About 5.75 cm. Width: About 3 cm. Shape: Ovate with acuminate apex, attenuate base and crenate margin. Texture: Smooth. Color: Upper surface: 147A. Lower surface: 147B with red (close to 178A) blotches. Venation, upper surface: 147A. Venation, lower surface: 147B. Petiole: Size: Length: About 1.8 cm. Diameter: About 2 mm. Color: White with slight reddish tinge.

Flower description:

*Flower type and habit.*—Large orange flowers. Consistently double and symmetrical flowers. Freely and continuously flowering. Flower buds open similar to a rose in fullness. Flowers arise from leaf axils, terminal bud opening first. Usually ten flowers per lateral branch. Flowers positioned above or beyond the foliage and face upward or outward. Flowers self-cleaning.

*Time to flower.*—Flowering generally commences four to six weeks after planting.

*Flowering season.*—Year-round under greenhouse conditions. In the garden, flowering is continuous from spring until fall.

*Flower diameter.*—About 3.5 cm.

*Flower depth (height).*—About 1.5 cm.

*Flower buds.*—Size: Length: About 1.5 cm. Diameter: About 1 cm. Shape: Ovoid. Color: 39B.

*Petals/petaloids.*—Quantity: Numerous. Size (largest petals): Length: About 1.7 cm. Width: About 1.5 cm. Shape: Round or cordate with rounded or dentate apex, cuneate or obtuse base and entire margin. Texture: Satiny, smooth. Color: When opening, upper surface: Iridescent, 34A. When opening, lower surface: Iridescent, 39B. Mature, upper surface: Iridescent, 34A. Mature, lower surface: Iridescent, lighter than 39B. Fading to: Iridescent, 34A.

*Spur.*—Length: About 2.5 cm. Shape: Narrow and curved. Color: Light orange, darker orange at distal end.

*Peduncles.*—Length: About 3.25 cm. Angle: Upright to outwardly arching. Strength: Moderate. Color: 144A.

*Reproductive organs.*—None observed. Under optimal flowering conditions, reproductive organs are not observed as these structures develop into sterile petaloids. Without the development of functional reproductive organs, pollination and subsequent seed production are not observed.

Disease resistance: Under commercial conditions, resistance nor susceptibility to pathogens has not been observed.

CHART A

| CHARACTERISTIC | 'TIOGA TANGERINE' | 'ROSEBUD ORANGE' |
|---|---|---|
| GROWTH HABIT | Upright and mounded, triangular | Open habit, cascading and pendulous |
| PLANT HEIGHT | About 25 cm | About 17 cm |
| VIGOR | Vigorous | Moderate |
| BRANCHING HABIT | Freely, usually 8 lateral branches per plant, dense | Low to moderate, usually 5 lateral branches per plant, less dense |
| LATERAL BRANCH LENGTH | About 20 cm | About 23 cm |
| LATERAL BRANCH DIAMETER | About 13 cm | About 8 mm |
| LATERAL BRANCH STRENGTH | Strong | Weak |
| STEM COLOR | 146C with faint red spots and red areas at nodes | 145B with more intense red spots and red areas at nodes |
| LEAF LENGTH | About 5.75 cm | About 5 cm |
| LEAF WIDTH | About 3 cm | About 3.5 cm |
| LEAF COLOR, UPPER SURFACE | 147A | 147A |
| LEAF COLOR, LOWER SURFACE | 147B with red blotches | 147B with fainter red blotches |
| PETIOLE LENGTH | About 1.8 cm | About 1.6 cm |
| PETIOLE DIAMETER | About 2 mm | About 2.5 mm |
| FLOWERING HABIT | Flowers face upward or outward | Flowers face outward or downward |
| FLOWER DIAMETER | About 3.5 cm | About 4 cm |
| SPUR LENGTH | About 2.5 cm | About 3 cm |
| SPUR COLOR | Light orange, darker orange at distal end | Light green, red at distal end |
| PETAL SHAPE | Rounded or cordate | Rounded |
| PETAL APEX | Rounded or dentate | Rounded |
| PEDUNCLE LENGTH | About 3.25 cm | About 3.75 cm |
| PEDUNCLE ANGLE | Upright to outwardly arching | Outwardly arching to downward |
| PEDUNCLE STRENGTH | Moderate | Weaker |

It is claimed:

1. A new and distinct Double Impatiens plant named 'Tioga Tangerine', as illustrated and described.

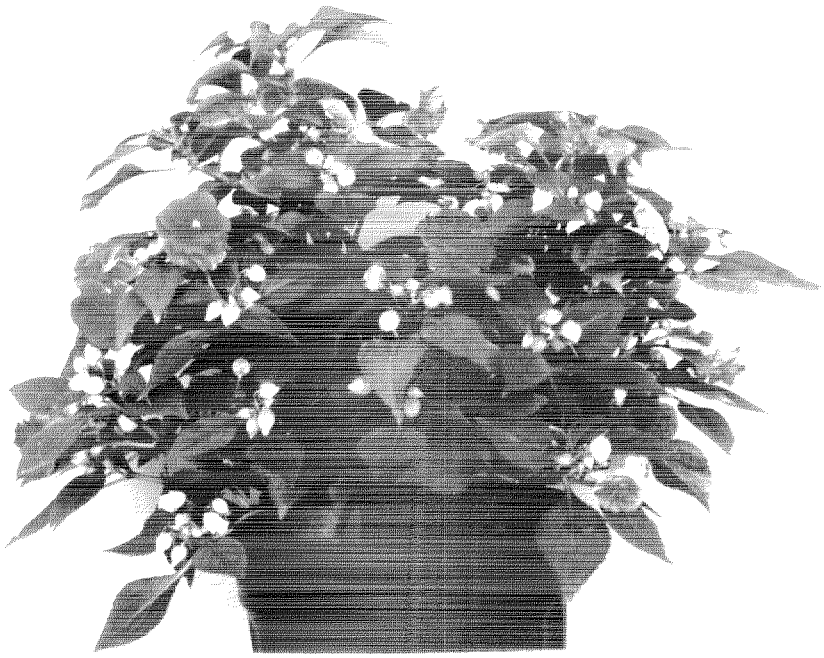
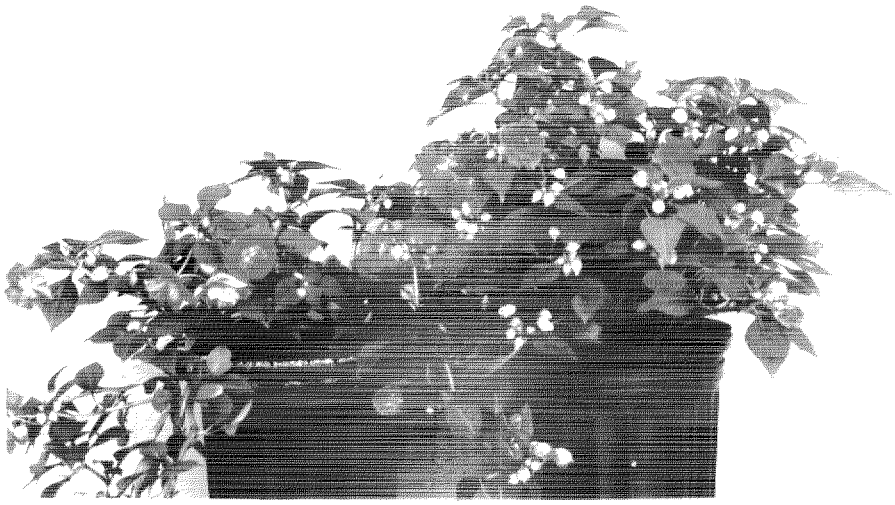

* * * * *